(12) United States Patent
Sugihara et al.

(10) Patent No.: US 6,835,813 B1
(45) Date of Patent: Dec. 28, 2004

(54) TESTIS-SPECIFIC DIFFERENTIATION-REGULATORY FACTOR

(75) Inventors: Takashi Sugihara, Ibaraki (JP); Renu Wadhwa, Ibaraki (JP); Sunil C. Kaul, Ibaraki (JP); Youji Mitsui, Ibaraki (JP)

(73) Assignees: Chugai Seiyaku Kabushiki Kaisha, Tokyo (JP); National Institute of Advanced Industrial Science & Technology, Tokyo (JP)

( * ) Notice: Subject to any disclaimer, the term of this patent is extended or adjusted under 35 U.S.C. 154(b) by 0 days.

(21) Appl. No.: 09/743,237

(22) PCT Filed: Jul. 16, 1999

(86) PCT No.: PCT/JP99/03859

§ 371 (c)(1),
(2), (4) Date: Jun. 4, 2001

(87) PCT Pub. No.: WO00/04147

PCT Pub. Date: Jan. 27, 2000

(30) Foreign Application Priority Data

Jul. 17, 1998 (JP) ............................................. 10-219856

(51) Int. Cl.[7] ............................................... C07K 14/47
(52) U.S. Cl. ....................................... 530/350; 530/400
(58) Field of Search ................................ 530/350, 400

(56) References Cited

U.S. PATENT DOCUMENTS 5,700,927 A * 12/1997 Zon et al. .................. 536/23.5

OTHER PUBLICATIONS

T. Sugihara et al., Genomics, vol. 57, "A Novel Testis–Specific Metallothionein–like Protein, Tesmin Is an Early Marker of Male Germ Cell Differentiation," pp. 130–136 (1999) Academic Press.

DATABASE: Homo sapiens cDNA clone IMAGE: 1394325, Mar. 10, 1998, NCI–CGAP: National Cancer Institute, Cancer Genome Anatomy Project Institute, Cancer Genome Anatomy Project (CGAP), Database accession No. AA84674 XP 002202236.

S.K. De et al., Mol. Endocrinol., vol. 5, "High level of metallothionein messenger RNAs in male germ cells of the adult mouse," pp. 628–636 (1991).

J.T. Deagen et al., Biochem. J., "Properties of cadium–binding proteins in rat testes. Characteristics unlike metallothionein," pp. 279–283 (1985).

P.E. Hunziker et al., Biochem. J. vol. 231, "Isolation and characterization of six human hepatic isometallothioneins," pp. 375–382 (1985).

I.M. McKenna et al., Toxicology, vol. 107, "Metallothionein gene expression in testicular interstitial cells and liver of rats treated," pp. 121–130 (1996).

C. Tohyama et al., Histochemistry, vol. 101, "Metallothionein mRNA in the testis and prostate of the rat detected by digoxigenin–labeled riboprobe," pp. 341–346 (1994).

M.P. Waalkes et al., J. Biol. Chem., vol. 261, "Isolation of a novel metal–binding protein from rat testes. Characterization and distinction from metallothionein," pp. 13097–13103 (1986).

* cited by examiner

*Primary Examiner*—Robert A. Wax
(74) *Attorney, Agent, or Firm*—Foley & Lardner LLP

(57) ABSTRACT

A gene expressed specifically in the testis has been unexpectedly isolated in the course of studies of the expression of a gene encoding an unknown protein that triggers cell death. The isolated gene was a novel gene sequence that had no significant homologue in the database. This gene was also found to be involved in the regulation of differentiation in the testis.

5 Claims, 9 Drawing Sheets

Tesmin-antisense primer

Tesmin-sense primer pEGFC1-complete Tesmin pEGFC1-Tesmin deletant

TESTIS-SPECIFIC DIFFERENTIATION-REGULATORY FACTOR

TECHNICAL FIELD

The present invention relates to a protein and its gene involved in the differentiation of testicular cells and belongs to the field of bioscience, specifically, developmental biology.

BACKGROUND ART

In the developmental process, reproductive cells carry out spermatogenesis via a differentiation process that includes meiosis. This differentiation process is different from that of somatic cells and consists of three main steps. The first step is the proliferation of spermatogenous cells and differentiation into primary spermatocytes. The second is the meiosis of primary spermatocytes, and the third is the transformation into sperms.

Owing to the progress in Molecular Biology, recent years have seen the isolation of several genes specifically expressed in these stages. For example, Hox-1.4 (Propst, F. et al. (1988) Oncogene 2:227–33), ferT (Sarge, K. D. et al. (1994) Biol Reprod 50:1334–1343) of the HSP70 family, and TESK1 (Toshima, J. et al. (1995) J. Biol. Chem. 270:31331–31337) that is a serine-threonine kinase, have been reported as genes specific to primary spermatocytes. However, still very little is known about the biological and physical roles of their gene products.

Genes expressing specifically in the differentiation process of reproductive cells carry a fundamental and vital role that decides the fate of those cells, and thus, defects in these genes are considered to be a cause of diseases such as infertility. Therefore, genes expressing specifically in the differentiation process of reproductive cells are recently gaining wide attention as targets in the development of pharmaceutical drugs. Such drugs can be used for the prevention and treatment of diseases such as infertility caused by defects in reproductive cell differentiation.

DISCLOSURE OF THE INVENTION

The present invention provides a novel protein relating to the differentiation of testicular cells, and the encoding gene. It also provides a vector and transformant used for, for example, producing the protein, and a method of producing the protein. The present invention also provides an oligonucleotide used for the isolation and the detection of the gene of the invention.

The inventors were evaluating the expression of genes encoding unknown proteins that trigger cell death when, irrelevant to their original aim, they unexpectedly succeeded in isolating a novel gene specifically expressed in the testis. When the databases were searched for the isolated gene, it was found to be a novel gene that did not have a significant homologous gene. Structural analysis of the protein encoded by the gene showed that it had in part a structure similar to the metal-binding site of metallothionein, which is known to be a metal-binding factor. Expression analysis in tissues revealed that the gene is extremely specific to the testis, especially to primary spermatocytes. The expression was not seen in the testis of infertile mice. Analysis of the human and mouse chromosomal locations showed that the gene was located in the same site as the gene locus that is known to be defective in infertile mice. Results of these analyses suggest that the protein encoded by the isolated gene is involved in regulating the differentiation of the testis.

The present invention relates to a novel protein involved in the regulation of testicular differentiation having a metal-binding site, and the gene thereof, more specifically:

(1) a protein comprising the amino acid sequence of SEQ ID NO: 4 or 5;

(2) a protein which comprises an amino acid sequence in which one or more amino acids in the amino acid sequence of SEQ ID NO: 4 or 5 have been replaced, deleted, and/or added, and which is functionally equivalent to the protein of (1);

(3) a protein which is encoded by a DNA hybridizing to the DNA comprising the nucleotide sequence of SEQ ID NO: 1 or 3, and which is functionally equivalent to the protein of (1);

(4) a DNA encoding the protein of any one of (1) to (3);

(5) a vector comprising the DNA of (4);

(6) a transformant comprising the DNA of (4) in an expressible manner;

(7) a method of producing the protein of any one of (1) to (3) comprising the steps of culturing the transformant of (6), and collecting the expressed protein from said transformant or the culture supernatant thereof;

(8) an antibody binding to the protein of any one of (1) to (3); and, (9) a DNA specifically hybridizing to a DNA comprising the nucleotide sequence of any one of SEQ ID NOs: 1 to 3, and comprising at least 15 nucleotides.

The present invention provides the protein Tesmin, which may regulate the differentiation of spermatogenous cells into primary spermatocytes, and the gene thereof.

The inventors isolated two types of Tesmin cDNA of mouse origin arising possibly from splicing differences in the transcriptional process. The nucleotide sequences of these cDNAS are shown in SEQ ID NOs: 1 and 2, and the amino acid sequence of the protein encoded by these cDNAs in SEQ ID NO: 4. The nucleotide sequence of human Tesmin cDNA also isolated by the inventors is shown in SEQ ID NO: 3, and the amino acid sequence of the protein encoded by the cDNA is shown in SEQ ID NO: 5.

As shown in SEQ ID NOs: 1 and 2, mouse-derived Tesmin cDNA has an ORF encoding a protein comprising 295 amino acids. On the other hand, human-derived Tesmin cDNA has an ORF encoding a protein comprising 299 amino acids, as shown in SEQ ID NO: 3. SDS-PAGE analysis of the in vitro translational product of mouse Tesmin using $^{35}$S-labeled methionine showed that mouse Tesmin protein had a molecular weight of 32.5 kDa (FIG. 3).

Among the tissues within the body, both mouse and human Tesmin genes were expressed only in the testis, as revealed by Northern blot analysis and RT-PCR (FIGS. 1 and 2). RT-PCR analysis showed that Tesmin gene is hardly expressed in the immature testis up to day 8 following birth, but the expression increases from day 12 when the sperm differentiation starts, and its high expression stabilizes from day 18. In the W/Wv mouse known as an infertile mouse that lacks the growth factor receptor "c-kit" gene, Tesmin gene expression was hardly seen even in the matured testis of day 52 following birth (FIG. 4). These facts suggest that the Tesmin protein is involved in the differentiation of the testis. The Tesmin protein and its gene can be applied, for example, in the treatment of infertility.

The Tesmin protein of the invention can be prepared by incorporating DNA encoding the protein (e.g., DNA comprising the nucleotide sequence of any one of SEQ ID NO: 1 to 3) into a suitable vector, introducing this into a suitable host cell, and purifying the protein from the transformant obtained. The protein of the present invention can also be prepared as a recombinant protein made using genetic engineering techniques by culturing cells transformed with DNA encoding the Tesmin protein, as mentioned later. The natural protein can be isolated from testicular tissues by methods well known to one skilled in the art, for example, the affinity chromatography later described, using an antibody that binds to the Tesmin protein.

A skilled artisan can prepare not only a natural Tesmin protein, but also a modified protein functionally equivalent to the natural protein by, for example, suitably performing amino acid substitution of the protein using known methods. Amino acid mutations of a protein can occur spontaneously, too. Therefore, the protein of the invention includes a mutant in which the amino acid sequence of the natural protein was mutated by, for example, replacing, deleting, or adding one or several amino acids, and which is functionally equivalent to the natural protein. Methods well known to a skilled artisan for modifying amino acids are, for example, PCR-mediated site-specific-mutation-induction system (GIBCO BRL, Gaithersburg, Md.), oligonucleotide-mediated site-specific-mutagenesis (Kramer, W. and Fritz, H J (1987) Methods in Enzymol. 154:350–367), the Kunkel method (Methods Enzymol. 85:2763–2766 (1988)), and so on. The number of amino acids mutated is normally within ten amino acids, preferably within six amino acids, and more preferably within three amino acids.

Herein, "functionally equivalent" means that the mutant protein has a biochemical and/or biological activity equivalent to the natural protein. As such activities, for example, the binding activity between the protein and metal, and the testicular cell differentiation-inducing activity can be given.

The metal-binding activity can be detected, for example, as follows. First, the recombinant Tesmin protein is EDTA-treated to remove heavy metals that may be bound to the Tesmin protein. Next, EDTA is removed by gel filtration, and then, the heavy metals (for example, $Zn^{2+}$, $Cd^{2+}$, $Cu^{2+}$, etc.) to be examined are added and reacted with the;recombinant Tesmin protein. After reacting, the presence or absence of a metal bond is detected as CD spectra using a CD spectropolarimeter (J-500C by Jasco) (refer Presta A. et al., Eur. J. Biochem Jan 15; 227(1–2):226–240).

The testicular cell differentiation-inducing activity can be detected, for example, as follows. First, spermatogoniums, spermatogenous cells, and primary spermatocytes are isolated from mouse testis by centrifugation. Next, Tesmin gene is incorporated into an expression vector (e.g., pBK-CMV vector, Stratagene), and the gene incorporated is introduced to cells isolated by lipofectAMINE (GIBCO BRL). After culturing the cells from a few hours to a few days, the expression of a genetic marker that identifies the differentiation stage (e.g., MEG1, ssH2B, etc.) is verified by the RT-PCR method.

The hybridization technique (Sambrook, J et al., Molecular cloning $2^{nd}$ed. 9.47–9.58, Cold Spring Harbor Lab. press, 1989) is well known to a skilled artisan as an alternative method for isolating a functionally equivalent protein. In other words, it is a general -procedure for a skilled artisan to isolate DNA having a high homology to the whole or part of the DNA encoding the mouse or human Tesmin protein (a DNA comprising the nucleotide sequence of any one of SEQ ID NOs: 1 to 3) and to obtain a protein functionally equivalent to the mouse or human Tesmin protein from the isolated DNA. Therefore, the protein of the present invention also includes a protein encoded by DNA hybridizing to DNA encoding the mouse or human-derived Tesmin protein, which is functionally equivalent to these proteins. When isolating the hybridizing DNA from other organisms, there is no restriction as to the organisms used, although testicular tissues from, for example, rats, rabbits, and cattle are suitable for the isolation. DNA isolated by hybridization techniques usually has a high homology to DNA encoding the mouse- and human-derived Tesmin protein (DNA comprising the nucleotide sequence of any one of SEQ ID NOs: 1 to 3). "High homology" means, a sequence identity at the amino acid level of at least 40% or more, preferably 60% or more, more preferably 80% or more, and even more preferably, 95% or more. The homology of a sequence can be calculated, for example, by the method described in Proc. Natl. Acad. Sci. USA (1983) 80:726–730.

An example of hybridization conditions (stringent) for isolating a DNA high in homology is as follows. Namely, after conducting a prehybridization at 68° C. for 30 min or more using the "Rapid-hyb buffer" (Amersham LIFE SCIENCE), a labeled probe is added, and hybridization is done by incubating at 68° C. for 1 hr or more. After that, washing is done three times within 2×SSC/0.01% SDS for 20 min at room temperature, and next, three times within 1×SSC/0.1% SDS, at 37° C. for 20 min, followed by, two times within 1×SSC/0.1% SDS, at 50° C. for 20 min.

This invention also provides a DNA encoding the Tesmin protein. The DNA of the present invention includes genomic DNA, synthetic DNA, and such, as well as cDNA, as long as such DNA encodes the Tesmin protein of the invention. The DNA of the invention can be used, for example, for producing recombinant proteins. Namely, the recombinant proteins can be prepared by inserting the DNA of the invention (e.g., SEQ ID NOs: 1 and 2) into a suitable expression vector, introducing this into a suitable cell, culturing the resulting transformant, and purifying the protein expressed. Cells used for the production of recombinant proteins are, for example, mammalian cells such as COS cells, CHO cells, and NIH3T3 cells; insect cells such as Sf9 cells; yeast cells; and E.coli, but there is no restriction as to the cells used. The vector for expressing the recombinant protein within cells varies according to the host cell, and, for example, pcDNA3 (Invitrogen), and pEF-BOS (Nucleic Acids. Res. 1990, 18 (17), p5322) and such are given as vectors for mammalian cells, Bac-to-BAC baculovirus expression system (GIBCO BRL) and such for insect cells, Pichia Expression Kit (Invitrogen) and such for yeast cells, and pGEX-5X-1 (Pharmacia) and QIAexpress system (Qiagen) and such for E.coli. Vectors can be introduced into hosts for example, by the calcium phosphate method, DEAE dextran method, the method using cationic liposome DOTAP (Boehringer Mannheim), electroporation method, calcium chloride method, etc. Transformants can be cultured according to their properties using methods well known to skilled artisans. Recombinant proteins can be purified from transformants by methods well known to skilled artisans, for example, the methods described in reference "The Qiaex-pressionist handbook, Qiagen, Hilden, Germany."

The present DNA can be used for gene therapy of diseases caused by mutations of the gene. The Tesmin gene especially may be the causative of the genetic disease of infertile mice, and therefore, is expected to be applied in the gene therapy of infertility. When using for gene therapy, the DNA of the invention is inserted into, for example, a viral vector such as an adenovirus vector (e.g. pAdexLcw) and a retrovirus vector. (e.g. pZIPneo), or a non-viral vector, and administered to a target site of the body. The method of administration may be ex vivo or in vivo.

The present invention also provides an antibody that binds to the protein of the invention. The antibody of the present invention includes polyclonal antibodies and monoclonal antibodies. These antibodies can be prepared by following methods well known to skilled artisans. Polyclonal antibodies can be made by, for example, obtaining the serum of small animals such as rabbits immunized with the protein (or a partial peptide) of the present invention, and purifying by, for example, ammonium sulfate precipitation, a protein A or protein G column, etc. Monoclonal antibodies can be made by immunizing small animals such as mice with the protein (or a partial peptide) of the present invention, excising the spleen from the animal, homogenizing the organ into cells, fusing the cells with mouse myeloma cells using a reagent such as polyethylene glycol, selecting clones that produce antibodies against the protein of the invention from the fused cells (hybridomas), transplanting the obtained hybridomas into the abdominal cavity of a mouse, and collecting ascites from the mouse. The obtained monoclonal antibodies can be purified by, for example, ammonium sulfate precipitation, a protein A or protein G column, etc. The antibody thus prepared can be applied for antibody therapy and such, other than for the purification and detection of the protein of the invention. When administrating the antibody to humans with the aim of antibody therapy, humanized antibodies are effective in decreasing immunogenicity. Antibodies can be humanized by, for example, cloning the antibody gene from monoclonal antibody producing cells and using the CDR graft method which transplants the antigen-recognition site of the gene into a known human antibody. Human antibodies can also be prepared like ordinary monoclonal antibodies by immunizing a mouse whose immune system has been replaced by a human immune system with the protein of the invention.

This invention also provides a DNA specifically hybridizing to DNA encoding the Tesmin protein and comprising at least 15 nucleotides. The term "specifically hybridizing" as used herein indicates that cross-hybridization does not significantly occur with DNA encoding proteins other than the Tesmin protein, under the usual hybridization conditions, preferably under stringent hybridization conditions. Such DNA can be used as a probe for detecting or isolating DNA encoding the Tesmin protein, or as a primer for amplification. Tesmin gene is expressed only in the testis, and even in the testis, it is expressed for a limited period. Therefore, the DNA can be used as a testis differentiation marker (a test drug). Also, there is a possibility that the Tesmin gene is the causative gene of the genetic disease of infertile mice, and therefore, the DNA may be used for the testing of infertility.

BEST MOLD FOR CARRYING OUT THE INVENTION

Figure 1:
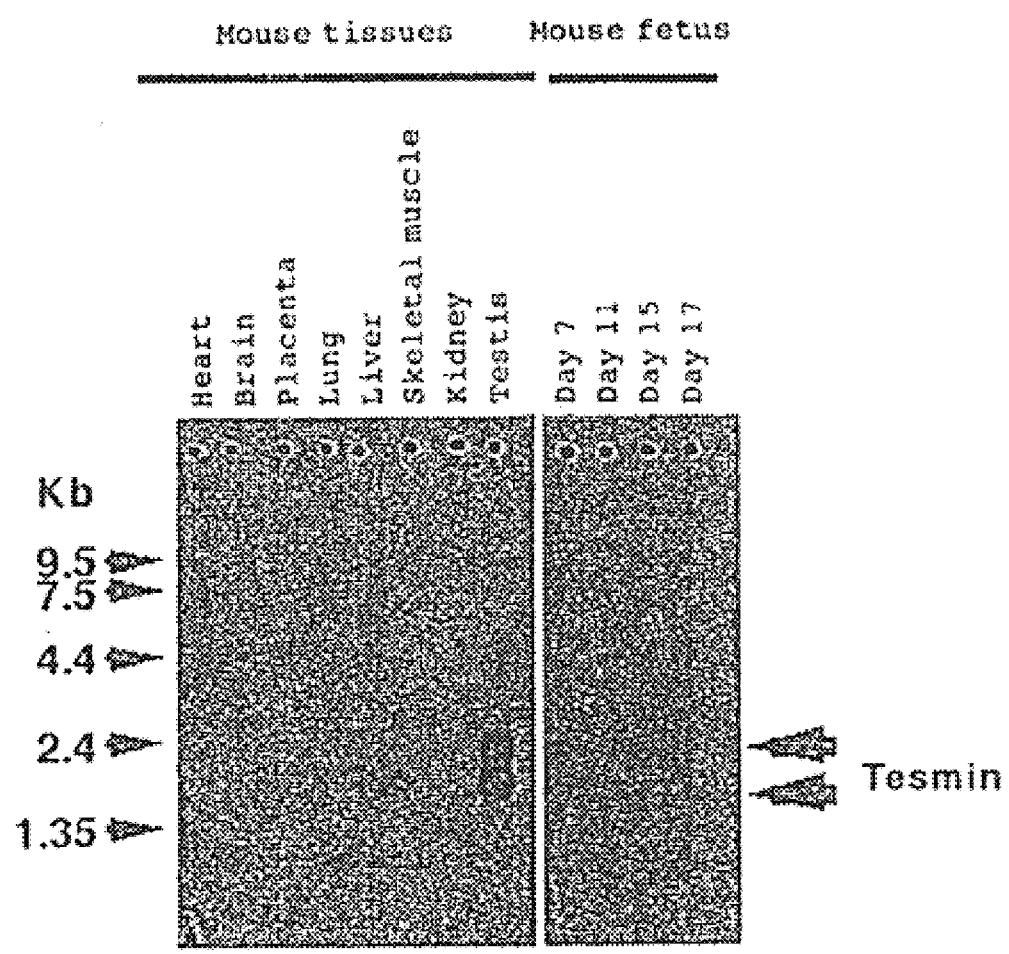
FIG. 1 is an electrophoretic photograph showing the results of Northern blot analysis of Tesmin gene expression in various mouse tissues.

The invention shall be specifically described in examples below, but it is not to be construed as being limited thereto.

EXAMPLE 1

Isolation of Tesmin Gene Fragment Using RT-PCR

The expression of the novel substance WF-1 (a function-unknown novel gene comprising 1700 bp) in each organ was analyzed by the RT-PCR method. Specifically, total RNA was extracted from the brain, liver, spleen, kidney, heart, and testis of ICR strain mice (Clea Japan) using ISOGEN (NIPPON GENE). After denaturing RNA at 65° C., cDNA was prepared using reverse transcriptase: superscript 2 (GIBCO BRL) using cDNA from each organ, and the oligo primers for WF-1 amplification described in SEQ ID NOs: 6 and 7, PCR reaction was conducted for 32 cycles of 94° C. for 1 min, 58° C. for 2 min, and 72° C. for 3 min. The control GAPDH was amplified by PCR using the oligo primers described in SEQ ID NOs: 8 and 9 under the condition of 30 cycles of 94° C. for 1 min, 58° C. for 2 min, and 72° C. for 3 min. As a result, a gene specifically expressed only in the testis was unexpectedly found through a detection using oligo primers for WF-1 amplification described in SEQ ID NOs: 6 and 7. This cDNA fragment was isolated, and the gene encoded by the cDNA was named "Tesmin" (first named "Testin," but later changed to "Tesmin").

EXAMPLE 2

Cloning and Sequencing of Mouse Tesmin cDNA

The sequence of the above cDNA fragment was determined by the dideoxy chain termination method and analyzed by the ABI377 auto sequencer. As a result of a database search for the determined sequence, this sequence was revealed to be a novel gene that did not have a homology to genes in the databank. This cDNA fragment was $^{32}P$ radio-labeled to prepare a probe, and using this, a mouse testis library was screened. As a result, a clone having an approximately 1.7 kb length was obtained.

Moreover, 5'-RACE was conducted to determine the 5' end sequence. In 5'-RACE, three antisense primers specific to the Tesmin gene, namely, SP1 (SEQ ID NO: 10), SP2 (SEQ ID NO: 11), and SP3 (SEQ ID NO: 12), and mouse testis-derived 5'-Marathon RACE cDNA were used. 5'-RACE method was conducted following the "Marathon-Ready™ cDNA kit (mouse testis)" (Clontech) protocol. The whole nucleotide sequence of Tesmin cDNA obtained is shown in SEQ ID NOs: 1 (2241bp) and2 (1861 bp). These two cDNAs are thought to be splicing variants arising from a difference in splicing at the point of transcription.

When the database was searched using these cDNA sequences, no sequence comprising a significant homology was found in the databank. These cDNAs encode the same protein comprising 295amino acids (pI-7.64), and no significantly homologous proteins were found in the protein database as well.

EXAMPLE 3

Cloning and Sequencing of Human Tesmin cDNA

Mouse Tesmin plasmid (a plasmid in which the Tesmin gene has been inserted into the pBluescript2 vector) was cleaved by SphI-SalI, and this 1.7 kb gene fragment was used as a probe to screen the cDNA library prepared by human testis MRNA. Hybridization was done using the "Rapid-hyb buffer" (Amersham LIFE SCIENCE) under the following conditions: (i) a prehybridization at 60° C. for 30 min, (ii) addition of the labeled probe, and (iii) hybridization by incubating at 60° C. for 2 hr. After that, washing is done three times within 2×SSC, 0.01% SDS for 20 min at room temperature, and next, three times within 1×SSC, 0.1% SDS, at 37° C. for 20 min, followed by, two times within 1×SSC, 0.1% SDS, at 50° C. for 20 min.

The nucleotide sequence of thus obtained human Tesmin cDNA is shown in SEQ ID NO: 3. Database search for the determined nucleotide sequence was done but there were no homologous sequences within the databank, similar to the mouse cDNA. The obtained human cDNA had four amino acids more than mouse Tesmin and encoded a protein comprising 299 amino acids (pI-7.71). No significant homology was found in the protein database as well. However, as a result of amino acid sequence analysis by BLAST, the mouse and human Tesmins were found to be cysteine-rich proteins partially having the structure very similar to the metal-binding domain of the metallothionein family.

Metallothionein expression in the liver is induced by heavy metals, and metallothionein is known as a protein that neutralizes metallic poison. However, in the testis, the metallothionein gene is constantly expressed and is not induced by metals. Therefore, it was thought to play some vital roles other than metal binding in the testis. Recent findings showed that the estrogen receptor, which is a zinc-finger transcription factor and a receptor protein, and metallothionein conduct metal transfer in vitro (Cano-Gauci, D. and Sarkar, B. (1996) FEBS Lett 386 (1):1–4). Therefore, the metal-binding site of metallothionein is thought to play a vital role in the regulation of transcription factors. The "Cys-X-Cys-X-X-X-X-X-X-X-X-X-Cys-X-Cys (where X is an arbitrary amino acid)" sequence having a cysteine structure in the amino acid sequence is thought to be vital for metal binding in the metallothionein family.

This cysteine structure (in mouse, from the $157^{th}$ to the $171^{st}$ positions, in human, from the $16^{st}$ to the $175^{th}$ positions) was conserved in Tesmin too. However, the metallothionein family members known up to now were relatively low-molecular comprising 60 to 70 amino acids, whereas Tesmin was comparatively longer (mouse: 295 amino acids, human: 299 amino acids). Domain search by PROSITE revealed that mouse Tesmin had a N-myristylation site and a casein kinase 2 phosphorylation site. Human Tesmin had a cAMP and cGMP-dependent kinase phosphorylation site, a protein kinase C phosphorylation site, a N-myristylation site, and a N-glycosylation site. Other than those, a CAMP and cGMP-dependent protein kinase phosphorylation site and a protein kinase phosphorylation site were also present.

Domain search by BLOCKS revealed sites common to mouse and human Tesmins. Namely, "high potential iron-sulfate protein" (from $87^{th}$ to $103^{rd}$ positions in mouse, from $87^{th}$ to $103^{rd}$ positions inhuman), "Adenodoxin family" (iron-sulfate binding region) (from $177^{th}$ to $194^{th}$ positions in mouse, from $181^{st}$ to $198^{th}$ positions in human), "Alpha-2-mavrogloburin family thiolester region" (from $243^{rd}$ to $252^{nd}$ positions in mouse, from $247^{th}$ to $256^{th}$ in human), "Arrestins proteins" (from $267^{th}$ to $277^{th}$ positions in mouse, from $271^{st}$ to $281^{st}$ positions in human), "Ribosomal protein L14 proteins" (from $5^{th}$ to $26^{th}$ positions in mouse, from $5^{th}$ to $26^{th}$ positions in human), "Cooper amine oxidase topaquinone proteins" (from $81^{st}$ to $109^{th}$ positions in mouse, from $81^{st}$ to $109^{th}$ positions in human), and "VFWC domain proteins" (from $13^{th}$ to $19^{th}$ positions and from $105^{th}$ to $113^{th}$ positions in mouse, from $105^{th}$ to $113^{th}$ positions in human) were confirmed in mouse and human Tesmins. When sequence features were analyzed by PRINTS, both mouse and human Tesmins had a "Rhodopsin-like GPCR superfamily signature" (from $93^{rd}$ to $117^{th}$ positions, from $231^{st}$ to $252^{nd}$ positions, and from $232^{nd}$ to $253^{rd}$ positions in mouse, from $43^{rd}$ to $67^{th}$ positions and from $236^{th}$ to $257^{th}$ positions in human). EXAMPLE 4

Transcription and Translation in Vitro

Figure 3:
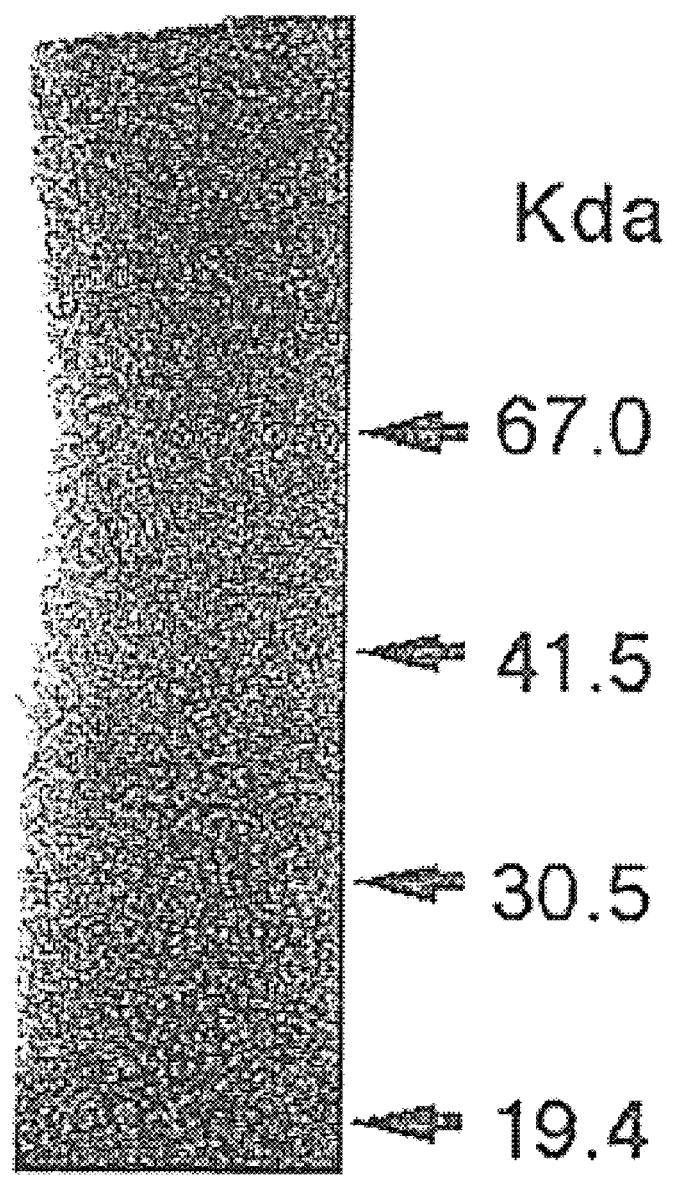
FIG. 3 is an electrophoretic photograph showing the results of the molecular weight detection of mouse Tesmin protein expressed by in vitro translation.

In vitro translation was done to verify the open reading frame anticipated in mouse Tesmin. Specifically, the cDNA pBluescript-Tesmin cloned from the testis was transcribed and translated for one hour in vitro using the rabbit reticulocyte lysate (Promega) to which L-[$^{35}$S] methionine has been added. Translation products were separated by SDS-PAGE, and detected by autoradiography. As a result, a protein of approximately 32.5 kDa was detected (FIG. 3). This product coincided well with the size of the protein thought to be the ORF within the mouse Tesmin sequence.

EXAMPLE 5

Preparation of Recombinant Tesmin

Figure 8:
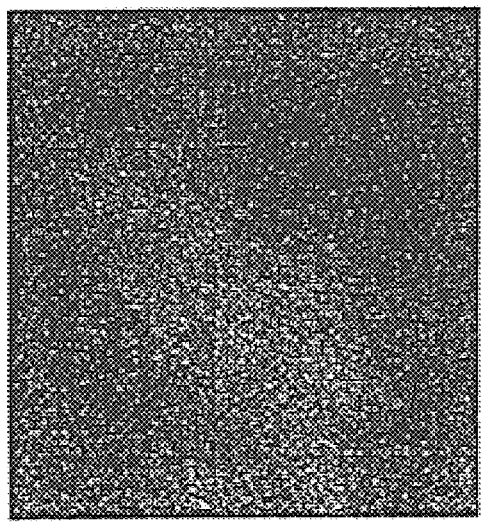
FIG. 8 is a photomicrograph showing the intracellular localization of the complete Tesmin protein and its deletion mutant.
Figure 8:
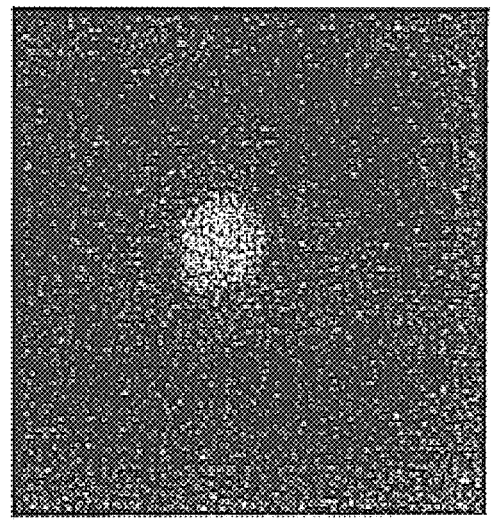

The open reading frame of mouse Tesmin cDNA was amplified by a PCR reaction using sense (SEQ ID NO: 19) and antisense (SEQ ID NO: 20) primers having an EcoRI site. The fragment amplified by the PCR reaction was cloned to the pGEM-T vector to verify its precise sequence. Next, it was cleaved by EcoRI-EcoRI, and finally cloned to pGEX-2TK vector that produces GST fusion protein. Tesmin product cloned into pGEX-2TK was gene transfected into E.coli JM109, induced using IPTG 0.2 mM at 37° C. for 3 hr. and the E.coli lysate was separated by SDS-PAGE, and detected by Western blotting using the GST antibody. As a result, a 58.5 kDa protein comprising a GST fusion portion with a molecular weight of 26 kDa was synthesized (FIG. 8 left). The recombinant protein had the same size expected by the presumed size of the molecule, similar to the result of in vitro translation.

EXAMPLE 6

Northern Blot Analysis

Figure 2:
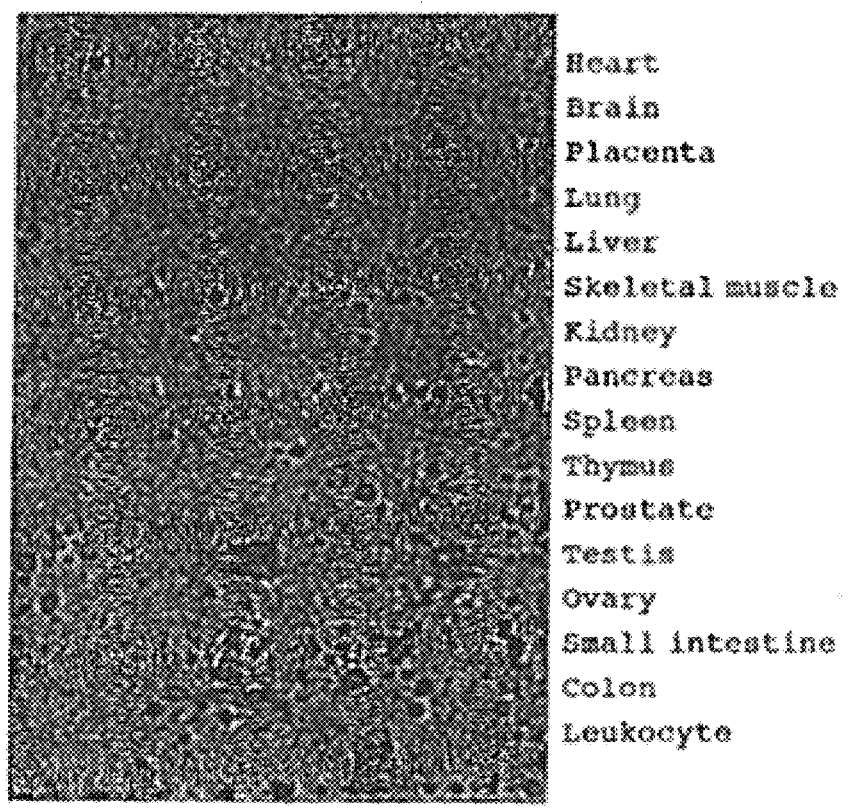
FIG. 2 is an electrophoretic photograph showing the results of Northern blot analysis of Tesmin gene expression in various human tissues.

A membrane loaded with 2 μg/lane of various mouse and human at tissue mRNA was purchased (Clontech laboratories, Palo alto, Calif.), and Northern blot analysis was conducted. The probe was a 1.7 kb gene fragment made by cleaving mouse Tesmin plasmid (a plasmid in which the Tesmin gene has been inserted into pBluescript2 vector) with SphI-SalI. Hybridization was done using the "Rapid-hyb buffer" (Amersham LIFE SCIENCE) under the following conditions: (i) a prehybridization at 68° C. for 30 min,(ii) addition of the labeled probe, and, (iii) hybridization by incubating at 68° C. for 2 hr. Next, washing is done three times within 2×SSC, 0.01% SDS for 20 min at room temperature, and next, three times within 1×SSC, 0.1% SDS, at 37° C. for 20 min, followed by, two times within 1×SSC, 0.1% SDS, at 50° C. for 20 min. Detection was done by autoradiography. Similar to the results of RT-PCR, Tesmin gene expression was detectable in the testis only, and gene expression was seen at the 2.4 kb and 2.0 kb locations in mouse (FIG. 1) and in just the 2.4 kb location in human (FIG. 2).

EXAMPLE 7

Involvement in the Differentiation of Reproductive Cells

Total RNA was extracted from the testis of ICR strain mouse at day 4, 8, 12, 18, and 42 following birth, and from the day 56 testis of W/Wv strain mouse (Japan SLC; type WBB6F1-W/Wv known as an infertile mouse deficient of the mouse growth factor S1 receptor c-kit gene; refer Chabot, B. et al. (1988) Nature 335 (6185):88–9, Yoshinaga, K. et al. (1991) Development 113 (2):689–99) using ISOGEN (NIPPON GENE). After denaturing this RNA at 65° C., cDNA was prepared using reverse transcriptase: superscript 2 (GIBCO BRL). Tesmin gene was amplified using the oligo primers described in SEQ ID NOs: 6 and 7, under the conditions of 35 cycles of 94° C. for 1 min, 58° C. for 2 min, and 72° C. for 3 min. The control GAPDH gene was amplified using the oligo primers described in SEQ ID NOs: 8 and 9, under the conditions of 30 cycles of 94° C. for 1 min, 58° C. for 2 min, and 72° C. for 3 min. For the MEG1 PCR reaction, the oligo primers described in SEQ ID NOs: 13 and 14 were used, under conditions of 35 cycles of 94° C. for 1 min, 58° C. for 2 min, and 72° C. for 3 min. For the ssH2B reaction, the oligo primers described in SEQ ID NOs: 15 and 16 were used, under the conditions of 35 cycles of 94° C. for 1 min, 58° C. for 2 min, and 72° C. for 3 min. Marker MEG1 expresses when spermatogenous cells divide into primary spermatocytes (Don, J. and Wolgemuth, D. J. (1992) August 3 (8):495–505), and marker ssH2B is known to express at spermatogenesis (Unni, E. et al. (1995) Biol Reprod, October 53 (4):820–826).

Figure 4:
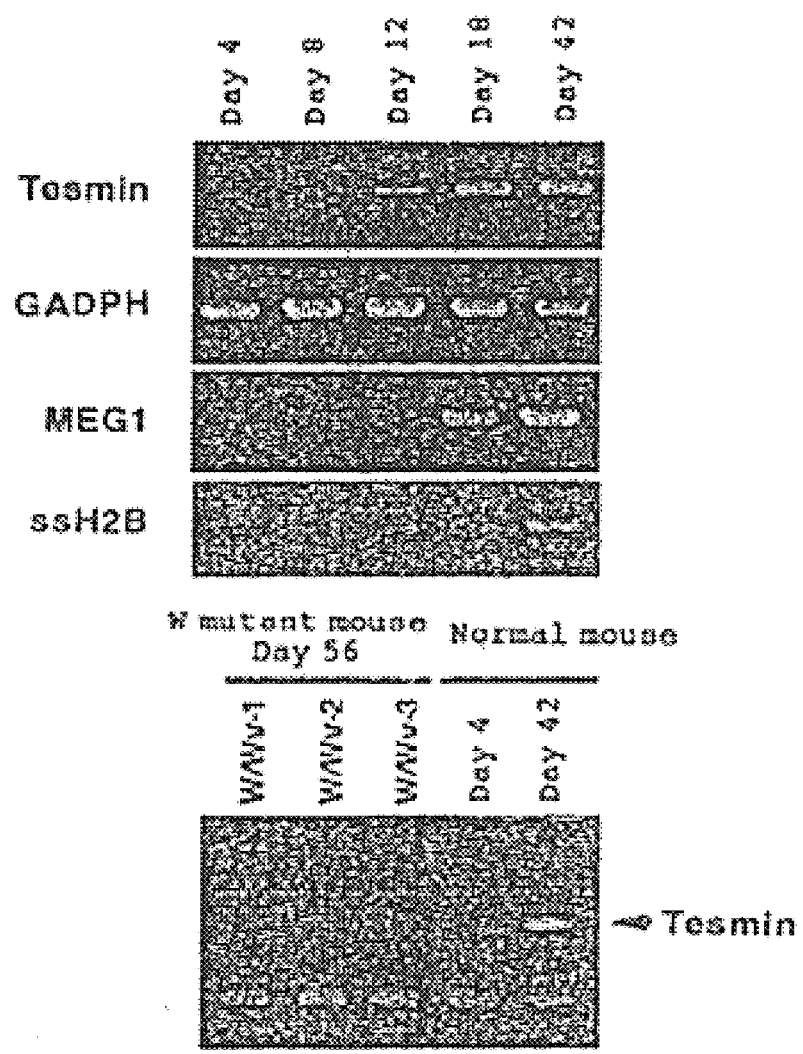
FIG. 4 is an electrophoretic photograph showing the results of Northern blot analysis of Tesmin gene expression in the testis of ICR strain mouse at day 4, 8, 12, 18, and 42 following birth, and in the day 56 testis of W/wv strain mouse. "MEG1" and "ssH2B" were used as testis differentiation markers. "GAPDH" was used as the control.

PCR analysis showed that Tesmin gene is not expressed until day 8 following birth, having a weak expression at day 12, and taking a stable expression pattern from day 18 (FIG. 4). Tesmin gene expression pattern in the testis was similar to MEG1. Therefore, it was revealed that Tesmin expression is regulated at time points similar to MEG1.

When Tesmin expression in the W/Wv mouse was examined, it was revealed that Tesmin is not expressed in these mice. Since the W/Wv mouse is known to be an infertile mouse, the relationship between Tesmin gene and infertility was strongly suggested (FIG. 4).

EXAMPLE 8

In Situ Hybridization

Figure 5:
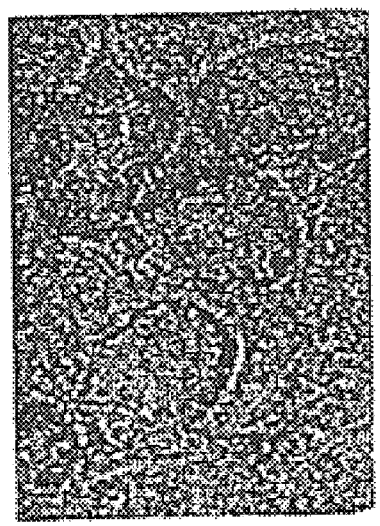
FIG. 5 is a photomicrograph showing the results of detection of Tesmin gene expression in testicular tissues by in situ hybridization.
Figure 5:
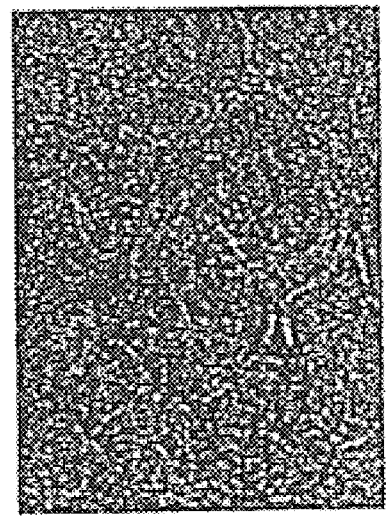

Labeled RNA probe was prepared from mouse Tesmin plasmid (the pBluescript2 vector in which the Tesmin gene has been inserted) using T7 and T3 polymerases and digoxigenin-dUTP. This probe was hybridized to sliced mouse testis tissue within a solution containing 50% formamide, 10% dextran sulfate, and 2×SSC. The slide glass on which hybridization was done was incubated within a solution of anti-digoxigenin antibody bound to alkaline phosphatase, and the signal specific to hybridization was detected using the chromogenic substrate NBT/BCIP. As a result, it was verified that Tesmin is extremely specifically expressed in the testis, especially in primary spermatocytes (FIG. 5).

EXAMPLE 9

Chromosomal Location

Mouse P1 genomic library was obtained by PCR screening the P1 bacteriophage genomic library using a mouse Tesmin-specific sense primer (SEQ ID NO: 6) and an antisense primer (SEQ ID NO: 7). Also, human P1 genomic library was obtained using human Tesmin-specific sense primer (SEQ ID No: 17) and antisense primer (SEQ ID NO: 18) and conducting a screening similar to mouse. The isolated P1 clones were used to examine the chromosomal localization by fluorescent in situ hybridization (FISH). Mouse and human P1 clone-derived DNA was labeled by nick translation using digoxigenin-dUTP, and this probe was hybridized to mouse and human primary fibroblast-derived metaphase chromosomes within a solution containing 50% formamide, 10% dextran sulfate, and 2×SSC. The slide glass on which hybridization was done was incubated within a solution of fluorescence-labeled anti-digoxigenin antibody, and the signal specific to hybridization was detected by counter staining using 4'6'-diamino-2-phenolindol (DAPI).

Figure 6:
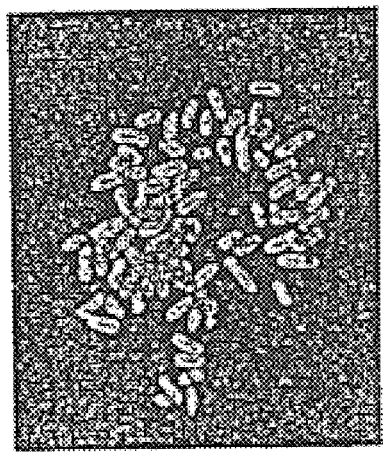
FIG. 6 is a photomicrograph and schematic diagram of the is chromosomal location-showing the results of the detection of Tesmin gene location in the mouse chromosome using a probe specific to the Tesmin gene.
Figure 6:
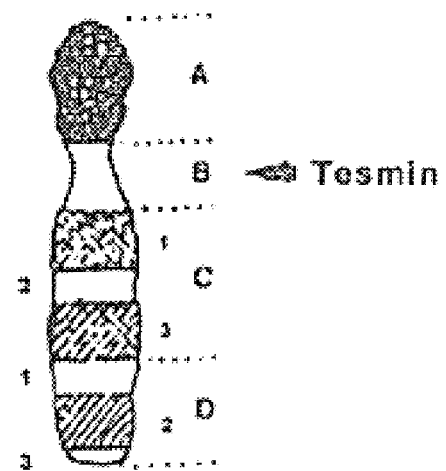
Figure 7:
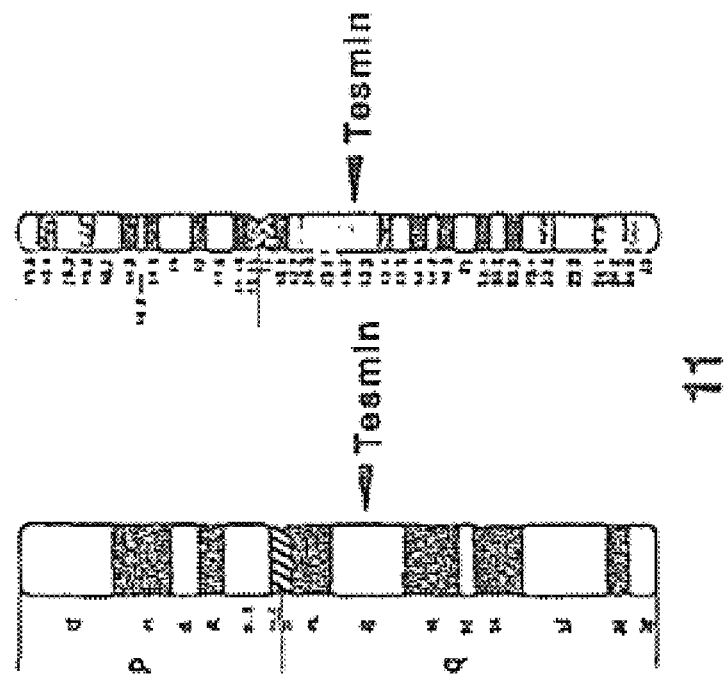
FIG. 7 is a photomicrograph and schematic diagram of the chromosomal location showing the results of the detection of Tesmin gene location in the human chromosome using a probe specific to the Tesmin gene.
Figure 7:
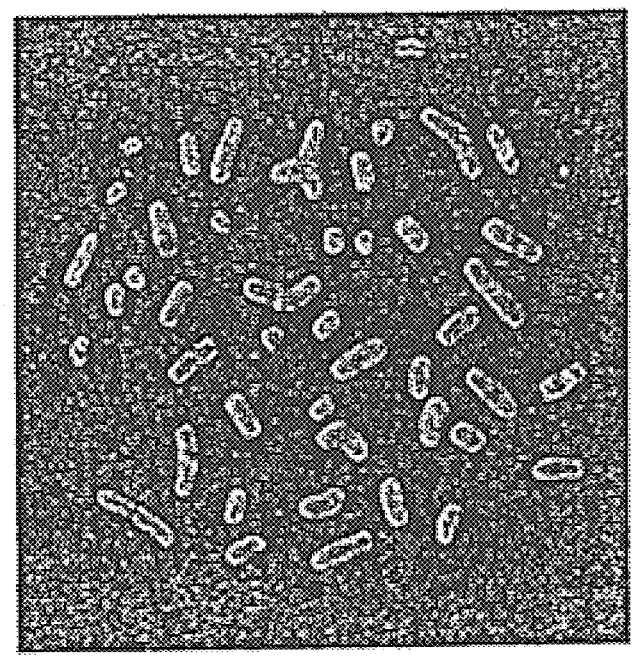

As a result, the above P1 clones were found to encode the Tesmin gene since the mouse and human Tesmin-specific probes hybridized to the respective P1 clone. When DAPI staining was done using these P1 clones as probes, the $19^{th}$ B chromosome and the $11^{th}$ q13.2 chromosome were specifically labeled in mouse and human, respectively. The above results confirmed that Tesmin was located on the $19^{th}$ B chromosome (FIG. 6) in mouse, and on the $11^{th}$ q13.2 chromosome (FIG. 7) in human. The relationship between Tesmin and mouse genetic disease was examined based on these results using the Jackson Laboratory Database to find that there is a study reporting that a mutation on the 19B chromosome where Tesmin exists causes infertility in mice (Evans, E P. (1977) Mouse News Letter, 17). This suggests the possibility that Tesmin mutations trigger infertility in mice.

EXAMPLE 10

Intracellular Localization

A DNA encoding whole open reading frame of the Tesmin cDNA were prepared, using sense (SEQ ID NO: 19) and antisense (SEQ ID NO: 20) primers having an EcoRI site, and also prepared was a gene designed so that 70 amino acids are deleted from the Tesmin cDNA open reading frame, by using a sense (SEQ ID NO: 19) primer having an EcoRI site and antisense (SEQ ID NO: 21) primer having an SalI site. These genes were treated with restriction enzymes and inserted into the C terminal region of GFP ORF of the pEGFC1 vector (Clontech). Using Tfx-50. (Promega), this plasmid that encodes the GFP-Tesmin fusion protein was introduced into COS1 cells growing on a cover glass. The cover glass was fixed by methanol/acetone (1:1) and washed three times with PBS. The cells were observed with Olympus BH-2 Epifluorescent Microscope. As a result, although the protein fused to the full sequence of Tesmin was localized within the cytoplasm, one having the partially deleted Tesmin sequence had migrated into the nucleus (FIG. 8).

EXAMPLE 11

Preparation of a Specific Antibody that Binds to the Tesmin Protein

A peptide antibody against the 18 amino acids presumed by the gene arrangement of Tesmin was prepared. Specifically, an 18 amino acid sequence (SEQ ID NO: 22) was made using a peptide synthesizer. KLH was covalently bound to this obtained peptide with a crosslinking reagent. Next, this peptide was purified by HPLC, and a rabbit was immunized with it. Serum was drawn out at four stages, and finally, all the blood was collected. This serum was purified using a protein A column to prepare the polyclonal antibody. Tesmin protein fused with GST was separated on a gel by SDS-PAGE. Detection by Western blotting confirmed that this anti Tesmin polyclonal antibody recognizes the Tesmin protein (FIG. 9).

Figure 9:
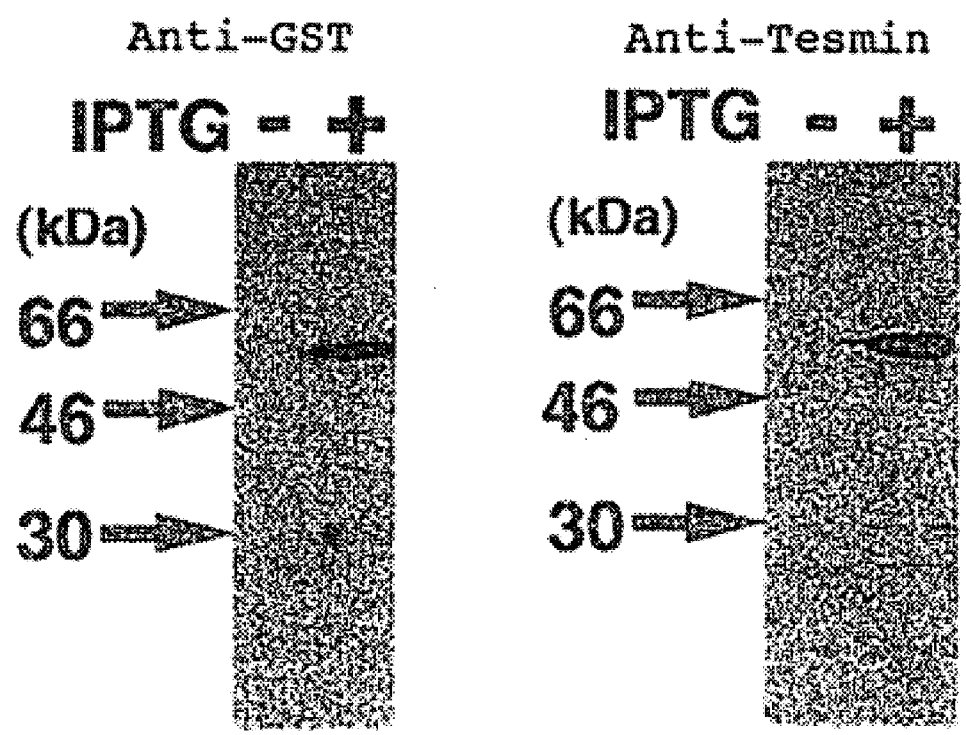
FIG. 9 shows the results of the detection of the Tesmin protein (fusion protein with GST) by Western blotting using the prepared anti Tesmin antibody. Detection using anti GST antibody was also done concurrently. "IPTG+" means the protein detected by adding isopropyl-β-D-thiogalactoside (IPTG) to cDNA-introduced E.coli to induce the expression of the recombinant protein, subjecting the cell lysate to SDS-PAGE and Western-blotting, and "IPTG-" means the protein detected in a lysate of E.coli to which IPTG was not added.

Western blotting was done by inducing recombinant protein expression through isopropyl-β-D-thiogalactoside (IPTG) added to Tesmin-cDNA-introduced E. coli, and subjecting an E. coli lysate to SDS-PAGE (IPTG+, FIG. 9). A detection using a cell lysate of E. coli without IPTG was also done (IPTG−, FIG. 9).

Industrial Applicability

The present invention provides the Tesmin protein comprising a metal-binding site, which is closely associated with the differentiation of testicular cells, and the gene thereof. The Tesmin protein and the gene thereof are involved in the differentiation during spermatogenesis, and Tesmin gene expression is not seen in infertile mice. Therefore, this gene may also be the causative gene of the genetic disease of infertile mice. Hence, it is anticipated that gene therapy of infertility would be possible by introducing the Tesmin gene into the body or cells. Moreover, Tesmin is expressed in the testis only, and even in the testis, the expression is seen only at limited stages. Therefore, Tesmin may also be applied as a test drug for determining the differentiation stage of testicular cells. Tesmin is also thought to contain a metal-binding site similar to metallothionein, and therefore, can also be applied as a metal-poison neutralizing agent similar to metallothionein. It is also expected to be utilized in applied studies such as those analyzing the importance of metal binding in the testis.

What is claimed is:

1. An isolated protein comprising the amino acid sequence of SEQ ID NO:4 or 5.

2. An isolated protein which comprises an amino acid sequence having 60% or more identity to the amino acid sequence of SEQ ID NO:4 or 5, wherein said protein has testicular cell differentiation activity.

3. An isolated protein which is encoded by a DNA hybridizing under the following conditions: prehybridize at 68° C. for at least 30 minutes, incubate at 68° C. for at least 1 hour, then wash three times with 2×SSC/0.01% SDS for 20 minutes at room temperature, and next, wash three times with 1×SSC/0.1% SDS, at 37° C. for 20 minutes, followed by two times with 1×SSC/0.1% SDS, at 50° C. for 20 minutes to the DNA comprising the nucleotide sequence of SEQ ID NO:1 or 3, wherein said protein has testicular cell diffferentiation activity.

4. The isolated protein of claim 2, which comprises an amino acid sequence having 80% or more identity to the amino acid sequence of SEQ ID NO:4 or 5.

5. The isolated protein of claim 2, which comprises an amino acid sequence having 95% or more identity to the amino acid sequence of SEQ ID NO:4 or 5.

* * * * *

SEQUENCE LISTING

```
<160> NUMBER OF SEQ ID NOS: 24

<210> SEQ ID NO 1
<211> LENGTH: 2241
<212> TYPE: DNA
<213> ORGANISM: Mus musculus
<220> FEATURE:
<221> NAME/KEY: CDS
<222> LOCATION: (651)..(1535)

<400> SEQUENCE: 1
tatcctgtgg gttggccccg ggcagcaggc tctcagcagg ctcaggcacc acaagggata      60
cacagtgtgt gttcctggcc tgttggactt gtgactccac ccacctccgc cccagcaggg     120
ctagggatag aacccagggc cttttgcgtg ttctgcagat agtcttcagc ctggtagttt     180
ggggttggct gggagatttt tttttcttca caccaaagac ttccattatt gaggattttt     240
tcagttgatg atctccccc tctgtaagat aagggacagt tcttaaacc tatgtagagt       300 tttgatgaat tctgcttctc aaccatattg ctaagctata tagcaattcc ttgaaattgc     360
tatataactt aggagaacct ctgattctcc tgcctctaca tcctgagtgc taggtgtaca     420
gggggaaatc attttggtga gactccgatg aactactgcc aggttcccaa ggcagcaagc     480
aagcaagaaa aagtgttgaa atcaaagaag caggtggtag tgtgccaggc ggcagccctg     540
aagacgcagc tttccaggcc cctctggctc aggaatcctg ttgcaagttc ccatcatccc     600
aggaggcaga ggaggcctcc agctgccctc ggaagaaaga ctccagcccc atg gtg        656
                                                          Met Val
                                                           1 att tgt cag ctg aaa gga ggc gcc cag atg ctc tgc ata gac aac tgt       704
Ile Cys Gln Leu Lys Gly Gly Ala Gln Met Leu Cys Ile Asp Asn Cys
         5                  10                  15 ggc gcg agg gag ctc aaa gcg ctc cat ctg ctt cct cag tac gat gac       752
Gly Ala Arg Glu Leu Lys Ala Leu His Leu Leu Pro Gln Tyr Asp Asp
     20                  25                  30
```

-continued

| | |
|---|---|
| cag agc agt ttc cct cag tca gag ctc cct aag cca atg aca act tta<br>Gln Ser Ser Phe Pro Gln Ser Glu Leu Pro Lys Pro Met Thr Thr Leu<br>35                          40                        45                          50 | 800 |
| gtg gga aga ctt ctg cca gta cca gcg aag tta aat ctc atc aca cag<br>Val Gly Arg Leu Leu Pro Val Pro Ala Lys Leu Asn Leu Ile Thr Gln<br>                        55                        60                        65 | 848 |
| gtt gat aat gga gct ctc cca tca gct gtc aat ggg gct gcc ttt ccc<br>Val Asp Asn Gly Ala Leu Pro Ser Ala Val Asn Gly Ala Ala Phe Pro<br>            70                        75                        80 | 896 |
| tct gga cct gct ctg caa ggg cca ccc aaa ata act ctg tct ggg tac<br>Ser Gly Pro Ala Leu Gln Gly Pro Pro Lys Ile Thr Leu Ser Gly Tyr<br>              85                        90                        95 | 944 |
| tgt gac tgc ttc tcc agc ggg gac ttc tgc aac agc tgc agc tgc aac<br>Cys Asp Cys Phe Ser Ser Gly Asp Phe Cys Asn Ser Cys Ser Cys Asn<br>100                          105                        110 | 992 |
| aac ctg cgc cat gag ctc gag cgc ttc aaa gcc ata aag gcg tgt ctt<br>Asn Leu Arg His Glu Leu Glu Arg Phe Lys Ala Ile Lys Ala Cys Leu<br>115                          120                        125                  130 | 1040 |
| gat aga aat cct gaa gct ttc caa cca aaa atg ggg aaa ggc cgt ctg<br>Asp Arg Asn Pro Glu Ala Phe Gln Pro Lys Met Gly Lys Gly Arg Leu<br>                        135                        140                        145 | 1088 |
| gga gct gct aaa ctt cga cac agc aaa ggg tgc aac tgt aag cgc tca<br>Gly Ala Ala Lys Leu Arg His Ser Lys Gly Cys Asn Cys Lys Arg Ser<br>              150                        155                        160 | 1136 |
| ggc tgc ctg aag aac tac tgt gag tgc tat gag gcc aaa atc atg tgt<br>Gly Cys Leu Lys Asn Tyr Cys Glu Cys Tyr Glu Ala Lys Ile Met Cys<br>            165                        170                        175 | 1184 |
| tct tcc att tgc aaa tgc att gct tgc aaa aac tat gaa gaa agt cca<br>Ser Ser Ile Cys Lys Cys Ile Ala Cys Lys Asn Tyr Glu Glu Ser Pro<br>180                          185                        190 | 1232 |
| gaa cga aaa atg ctg atg agc aca ccc cac tac atg gag cct ggg gac<br>Glu Arg Lys Met Leu Met Ser Thr Pro His Tyr Met Glu Pro Gly Asp<br>195                          200                        205                  210 | 1280 |
| ttt gag agc agc cat tat ttg tcc cca gcc aag ttc tca gga cct cca<br>Phe Glu Ser Ser His Tyr Leu Ser Pro Ala Lys Phe Ser Gly Pro Pro<br>              215                        220                        225 | 1328 |
| aaa ctg aga aaa aat agg cag gcc ttc tcc tgt atc tcc tgg gaa gta<br>Lys Leu Arg Lys Asn Arg Gln Ala Phe Ser Cys Ile Ser Trp Glu Val<br>              230                        235                        240 | 1376 |
| gtg gag gcc aca tgt gcc tgc ctg ctg gcc cag ggt gag gaa gca gag<br>Val Glu Ala Thr Cys Ala Cys Leu Leu Ala Gln Gly Glu Glu Ala Glu<br>                  245                        250                        255 | 1424 |
| cag gag cac tgt tcc cca agc ttg gct gag cag atg atc ctg gag gag<br>Gln Glu His Cys Ser Pro Ser Leu Ala Glu Gln Met Ile Leu Glu Glu<br>260                          265                        270 | 1472 |
| ttt gga agg tgc ctg tcg cag att ctc cac atc gag ttc aag tcc aag<br>Phe Gly Arg Cys Leu Ser Gln Ile Leu His Ile Glu Phe Lys Ser Lys<br>275                          280                        285                  290 | 1520 |
| ggg ctg aaa att gag tagcgtgcaa gctggtaaag gggaatgcct gtggcaagcc<br>Gly Leu Lys Ile Glu<br>              295 | 1575 |
| tcagccctgg gaatctgcac cgaggaagct ggtgcccagg gaggagcaga ggccgcgcat | 1635 |
| catggccagg tcagctgtga ggtctgagtg atctgcatgg tactggccag cctactcaag | 1695 |
| gtatcctaaa gtgcaagcag gcagagccac cctggggatg acactggcc ctcctgtccc | 1755 |
| tggggaggcc ctctggggac tccctgccct gcataaaaag aggtgatttt tctacttgtt | 1815 |
| gttatgtgtt tgctttcaaa ttgcttagta gtacctccat tcaagttatt atgagccagc | 1875 |

-continued

```
ctcaagttag agagctaggc tcttcttcag gtggactctg cccaaatcac atacaagtca    1935
ggtggccatc aggggttttt ccaggccagg cctgtgacag gagatatggg agggggggtcg   1995 ggttagagct gggtttgttt ggattttttg cgttttttc ttcctgtatt tctgcttgaa     2055
gtgagaaaac ttgtctcctg tccaacctttt tctccataat tactgctgca cggtcgcctg   2115
ctgaccagtc acagtgacct cagacaccag aaggtgaggt ggcttattat gcccacactt   2175
tgtgttttgt tgtgagaata aacctttcca gactcccaaa aaaaaaaaaa aaaaaaaaa    2235 aaaaaa                                                              2241
```

<210> SEQ ID NO 2
<211> LENGTH: 1861
<212> TYPE: DNA
<213> ORGANISM: Mus musculus
<220> FEATURE:
<221> NAME/KEY: CDS
<222> LOCATION: (271)..(1155)

<400> SEQUENCE: 2

```
ccagacgacg ccgctccgcc tcccgcctac agcgtgcacg tgttatcgtc gttacttccc     60
ggtgctcgcg ggcccgcgct gttgccgcta agcgcaggag tgcgcgtgat cccagttgaa    120
atcaaagaag caggtggtag tgtgccaggc ggcagccctg aagacgcagc tttccaggcc    180
cctctggctc aggaatcctg ttgcaagttc ccatcatccc aggaggcaga ggaggcctcc    240
agctgccctc ggaagaaaga ctccagcccc atg gtg att tgt cag ctg aaa gga    294
                                 Met Val Ile Cys Gln Leu Lys Gly
                                   1               5 ggc gcc cag atg ctc tgc ata gac aac tgt ggc gcg agg gag ctc aaa    342
Gly Ala Gln Met Leu Cys Ile Asp Asn Cys Gly Ala Arg Glu Leu Lys
 10                  15                  20 gcg ctc cat ctg ctt cct cag tac gat gac cag agc agt ttc cct cag    390
Ala Leu His Leu Leu Pro Gln Tyr Asp Asp Gln Ser Ser Phe Pro Gln
 25                  30                  35                  40 tca gag ctc cct aag cca atg aca act tta gtg gga aga ctt ctg cca    438
Ser Glu Leu Pro Lys Pro Met Thr Thr Leu Val Gly Arg Leu Leu Pro
             45                  50                  55 gta cca gcg aag tta aat ctc atc aca cag gtt gat aat gga gct ctc    486
Val Pro Ala Lys Leu Asn Leu Ile Thr Gln Val Asp Asn Gly Ala Leu
         60                  65                  70 cca tca gct gtc aat ggg gct gcc ttt ccc tct gga cct gct ctg caa    534
Pro Ser Ala Val Asn Gly Ala Ala Phe Pro Ser Gly Pro Ala Leu Gln
     75                  80                  85 ggg cca ccc aaa ata act ctg tct ggg tac tgt gac tgc ttc tcc agc    582
Gly Pro Pro Lys Ile Thr Leu Ser Gly Tyr Cys Asp Cys Phe Ser Ser
 90                  95                 100 ggg gac ttc tgc aac agc tgc agc tgc aac aac ctg cgc cat gag ctc    630
Gly Asp Phe Cys Asn Ser Cys Ser Cys Asn Asn Leu Arg His Glu Leu
105                 110                 115                 120 gag cgc ttc aaa gcc ata aag gcg tgt ctt gat aga aat cct gaa gct    678
Glu Arg Phe Lys Ala Ile Lys Ala Cys Leu Asp Arg Asn Pro Glu Ala
                125                 130                 135 ttc caa cca aaa atg ggg aaa ggc cgt ctg gga gct gct aaa ctt cga    726
Phe Gln Pro Lys Met Gly Lys Gly Arg Leu Gly Ala Ala Lys Leu Arg
            140                 145                 150 cac agc aaa ggg tgc aac tgt aag cgc tca ggc tgc ctg aag aac tac    774
His Ser Lys Gly Cys Asn Cys Lys Arg Ser Gly Cys Leu Lys Asn Tyr
        155                 160                 165 tgt gag tgc tat gag gcc aaa atc atg tgt tct tcc att tgc aaa tgc    822
Cys Glu Cys Tyr Glu Ala Lys Ile Met Cys Ser Ser Ile Cys Lys Cys
```

|   |   |   |   |   |   |   |   |   |   |   |   |   |   |   |   |   |
|---|---|---|---|---|---|---|---|---|---|---|---|---|---|---|---|---|
|   |   |   | 170 |   |   |   | 175 |   |   |   | 180 |   |   |   |   |   |
| att | gct | tgc | aaa | aac | tat | gaa | gaa | agt | cca | gaa | cga | aaa | atg | ctg | atg | 870 |
| Ile | Ala | Cys | Lys | Asn | Tyr | Glu | Glu | Ser | Pro | Glu | Arg | Lys | Met | Leu | Met |   |
| 185 |   |   |   |   | 190 |   |   |   |   | 195 |   |   |   |   | 200 |   |
| agc | aca | ccc | cac | tac | atg | gag | cct | ggg | gac | ttt | gag | agc | agc | cat | tat | 918 |
| Ser | Thr | Pro | His | Tyr | Met | Glu | Pro | Gly | Asp | Phe | Glu | Ser | Ser | His | Tyr |   |
|   |   |   |   |   | 205 |   |   |   |   | 210 |   |   |   |   | 215 |   |
| ttg | tcc | cca | gcc | aag | ttc | tca | gga | cct | cca | aaa | ctg | aga | aaa | aat | agg | 966 |
| Leu | Ser | Pro | Ala | Lys | Phe | Ser | Gly | Pro | Pro | Lys | Leu | Arg | Lys | Asn | Arg |   |
|   |   |   | 220 |   |   |   |   | 225 |   |   |   |   | 230 |   |   |   |
| cag | gcc | ttc | tcc | tgt | atc | tcc | tgg | gaa | gta | gtg | gag | gcc | aca | tgt | gcc | 1014 |
| Gln | Ala | Phe | Ser | Cys | Ile | Ser | Trp | Glu | Val | Val | Glu | Ala | Thr | Cys | Ala |   |
|   |   | 235 |   |   |   |   | 240 |   |   |   |   | 245 |   |   |   |   |
| tgc | ctg | ctg | gcc | cag | ggt | gag | gaa | gca | gag | cag | gag | cac | tgt | tcc | cca | 1062 |
| Cys | Leu | Leu | Ala | Gln | Gly | Glu | Glu | Ala | Glu | Gln | Glu | His | Cys | Ser | Pro |   |
|   | 250 |   |   |   |   | 255 |   |   |   |   | 260 |   |   |   |   |   |
| agc | ttg | gct | gag | cag | atg | atc | ctg | gag | gag | ttt | gga | agg | tgc | ctg | tcg | 1110 |
| Ser | Leu | Ala | Glu | Gln | Met | Ile | Leu | Glu | Glu | Phe | Gly | Arg | Cys | Leu | Ser |   |
| 265 |   |   |   |   | 270 |   |   |   |   | 275 |   |   |   |   | 280 |   |
| cag | att | ctc | cac | atc | gag | ttc | aag | tcc | aag | ggg | ctg | aaa | att | gag |   | 1155 |
| Gln | Ile | Leu | His | Ile | Glu | Phe | Lys | Ser | Lys | Gly | Leu | Lys | Ile | Glu |   |   |
|   |   |   |   | 285 |   |   |   |   | 290 |   |   |   |   | 295 |   |   |

|   |   |
|---|---|
| tagcgtgcaa gctggtaaag gggaatgcct gtggcaagcc tcagccctgg gaatctgcac | 1215 |
| cgaggaagct ggtgcccagg gaggagcaga ggccgcgcat catggccagg tcagctgtga | 1275 |
| ggtctgagtg atctgcatgg tactggccag cctactcaag gtatcctaaa gtgcaagcag | 1335 |
| gcagagccac cctggggatg gacactggcc ctcctgtccc tggggaggcc ctctggggac | 1395 |
| tccctgccct gcataaaaag agggtgattt tctacttgtt gttatgtgtt tgctttcaaa | 1455 |
| ttgcttagta gtacctccat tcaagttatt atgagccagc tcaagttag agagctaggc | 1515 |
| tcttcttcag gtggactctg cccaaatcac atacaagtca ggtggccatc aggggttttt | 1575 |
| ccaggccagg cctgtgacag gagatatggg aggggggtcg ggttagagct gggtttgttt | 1635 |
| ggattttttg cgtttttttc ttcctgtatt tctgcttgaa gtgagaaaac ttgtctcctg | 1695 |
| tccaacctttt tctccataat tactgctgca cggtcgcctg ctgaccagtc acagtgacct | 1755 |
| cagacaccag aaggtgaggt ggcttattat gcccacactt tgtgttttgt tgtgagaata | 1815 |
| aacctttcca gactcccaaa aaaaaaaaaa aaaaaaaaaa aaaaaa | 1861 |

<210> SEQ ID NO 3
<211> LENGTH: 2134
<212> TYPE: DNA
<213> ORGANISM: Homo sapiens
<220> FEATURE:
<221> NAME/KEY: CDS
<222> LOCATION: (407)..(1303)

<400> SEQUENCE: 3

|   |   |
|---|---|
| aattcggggt caaggcgaag ctcgcggggg gcgacagcga cggcgggag ctcctcgggg | 60 |
| agtaccccgg gatcccagag ctcagcgcgc tggaggacgt cgcgctcctg caggccccgc | 120 |
| agccgcccgc ctgcaacgtg cacttcctgt cctcgctgct acccgcgcac cgcagcccgc | 180 |
| gggtgttttg ccctgggggc gcctgggtcc tgcgaaggag cctcccaccc gggcgtccgc | 240 |
| atgatcccag ttgaaatcaa ggtaagcagg tggtactact acaagtaata atccggaaga | 300 |
| agcaactttg cagaatcttc ttgctcagga atcctgttgc aagttcccat ggtcccagga | 360 |
| actagaggat gcctcctgct gttctcttaa gaaagattcc aaccca atg gtg ata | 415 |
|   | Met Val Ile |

```
                                                                          1
tgc caa ttg aaa ggg ggc aca caa atg cta tgt ata gac aat tct aga           463
Cys Gln Leu Lys Gly Gly Thr Gln Met Leu Cys Ile Asp Asn Ser Arg
  5                  10                  15 aca aga gaa cta aaa gca ctc cat ttg gtt cct cag tat caa gat caa           511
Thr Arg Glu Leu Lys Ala Leu His Leu Val Pro Gln Tyr Gln Asp Gln
 20                  25                  30                  35 aat aat tat cta cag tca gat gtc cct aaa cca atg act gct tta gta           559
Asn Asn Tyr Leu Gln Ser Asp Val Pro Lys Pro Met Thr Ala Leu Val
                 40                  45                  50 ggg aga ttt ttg cca gca tca aca aaa tta aat ctc att aca caa caa           607
Gly Arg Phe Leu Pro Ala Ser Thr Lys Leu Asn Leu Ile Thr Gln Gln
             55                  60                  65 ctt gag gga gcc tta cca tcg gta gtc aac ggg tct gct ttc ccc tcg           655
Leu Glu Gly Ala Leu Pro Ser Val Val Asn Gly Ser Ala Phe Pro Ser
         70                  75                  80 gga tca act ctt cca gga cca cca aaa ata act ttg gct ggg tac tgt           703
Gly Ser Thr Leu Pro Gly Pro Pro Lys Ile Thr Leu Ala Gly Tyr Cys
     85                  90                  95 gac tgc ttt gcc agt ggg gac ttt tgc aac aac tgc aat tgt aat aat           751
Asp Cys Phe Ala Ser Gly Asp Phe Cys Asn Asn Cys Asn Cys Asn Asn
100                 105                 110                 115 tgt tgc aac aac ttg cat cat gat att gaa cgg ttt aaa gcc att aag           799
Cys Cys Asn Asn Leu His His Asp Ile Glu Arg Phe Lys Ala Ile Lys
                120                 125                 130 gca tgt ctt ggt aga aat cca gaa gct ttc cag cca aaa att ggg aag           847
Ala Cys Leu Gly Arg Asn Pro Glu Ala Phe Gln Pro Lys Ile Gly Lys
            135                 140                 145 ggc caa ttg ggc aat gtc aag ccc cag cac aac aaa ggg tgc aac tgc           895
Gly Gln Leu Gly Asn Val Lys Pro Gln His Asn Lys Gly Cys Asn Cys
        150                 155                 160 agg agg tca ggc tgc ctg aag aat tac tgc gag tgc tat gag gcc caa           943
Arg Arg Ser Gly Cys Leu Lys Asn Tyr Cys Glu Cys Tyr Glu Ala Gln
    165                 170                 175 att atg tgt tct tct att tgc aaa tgc att ggt tgc aaa aat tat gaa           991
Ile Met Cys Ser Ser Ile Cys Lys Cys Ile Gly Cys Lys Asn Tyr Glu
180                 185                 190                 195 gaa agc cca gaa cga aag aca cta atg agc atg cca aac tac atg cag          1039
Glu Ser Pro Glu Arg Lys Thr Leu Met Ser Met Pro Asn Tyr Met Gln
                200                 205                 210 act gga ggt ttg gaa ggc agc cat tac ctg cca cca acg aaa ttt tca          1087
Thr Gly Gly Leu Glu Gly Ser His Tyr Leu Pro Pro Thr Lys Phe Ser
            215                 220                 225 gga ctt cca aga ttc agt cac gat agg cgg cct tcc tca tgc atc tcc          1135
Gly Leu Pro Arg Phe Ser His Asp Arg Arg Pro Ser Ser Cys Ile Ser
        230                 235                 240 tgg gag gtg gtg gag gcc aca tgc gcc tgc ctg ctt gct cag gga gaa          1183
Trp Glu Val Val Glu Ala Thr Cys Ala Cys Leu Leu Ala Gln Gly Glu
    245                 250                 255 gag gcc gag aaa gaa cac tgc tcc aag tgc ctg gca gag cag atg atc          1231
Glu Ala Glu Lys Glu His Cys Ser Lys Cys Leu Ala Glu Gln Met Ile
260                 265                 270                 275 ctg gag gaa ttt gga agg tgc tta tca cag att ctc cac act gag ttt          1279
Leu Glu Glu Phe Gly Arg Cys Leu Ser Gln Ile Leu His Thr Glu Phe
                280                 285                 290 aaa tct aag gga ttg aaa atg gag tagagtataa agtgtgaatg catgttgatt         1333
Lys Ser Lys Gly Leu Lys Met Glu
            295 ttgtcttagt ctagaaatct ctagtttaga aaggatgttt aggggaacat gaggctggct        1393
```

-continued

```
ctgcagcaac aaccaggctc ccctgcatcc ctgggcccag ggagtttact cagagctctc   1453
tgaagatgtg gcaacccatg ccccttttc tgaggaggtg catggcctga gcattgtttg    1513
tctggcccag aggagagagc ttgggttccc atagtcctgg gagagtgtct gcagggcggc   1573
ggagggcaga gcaggccctg cggagagctc actctggtcg actcttcctc tcagagaatg   1633
ttgctctgga ggctgctctg catgaaaacc ctaatggttt cttgtttgtt tttcaaatta   1693
tttagaaata agttctccgg atgggctgtt gtgataccac ttaaaatctc tagagaacta   1753
ctgaacacct aaagattttc tgtagcgtag atatttcccc agagacacgc gaactgtcag   1813
tctttcctaa ggcccccggg agacgcaggc aatggggcct cgcaggccag gcttgcacca   1873
gcatgtcttg agttagagga cttaaaatta tccagtttct tctgtgtttc tacttgaatt   1933
gtggaaaagc tctattatcc aattaacttc tccataatta ttgttgtaat attattattg   1993
tttgtaaaac atggttcaca taactagctt gtggaaacca gcaggtaaaa tgaattctta   2053
agttgacgct tttggttctg ttgtaaagca aagatgaata aaaatttcca atgtcgaaaa   2113
aaaaaaaaaa aaaaaaaaa a                                             2134
```

<210> SEQ ID NO 4
<211> LENGTH: 295
<212> TYPE: PRT
<213> ORGANISM: Mus musculus

<400> SEQUENCE: 4

```
Met Val Ile Cys Gln Leu Lys Gly Gly Ala Gln Met Leu Cys Ile Asp
  1               5                  10                  15

Asn Cys Gly Ala Arg Glu Leu Lys Ala Leu His Leu Leu Pro Gln Tyr
             20                  25                  30

Asp Asp Gln Ser Ser Phe Pro Gln Ser Glu Leu Pro Lys Pro Met Thr
         35                  40                  45

Thr Leu Val Gly Arg Leu Leu Pro Val Pro Ala Lys Leu Asn Leu Ile
     50                  55                  60

Thr Gln Val Asp Asn Gly Ala Leu Pro Ser Ala Val Asn Gly Ala Ala
 65                  70                  75                  80

Phe Pro Ser Gly Pro Ala Leu Gln Gly Pro Lys Ile Thr Leu Ser
                 85                  90                  95

Gly Tyr Cys Asp Cys Phe Ser Ser Gly Asp Phe Cys Asn Ser Cys Ser
                100                 105                 110

Cys Asn Asn Leu Arg His Glu Leu Glu Arg Phe Lys Ala Ile Lys Ala
            115                 120                 125

Cys Leu Asp Arg Asn Pro Glu Ala Phe Gln Pro Lys Met Gly Lys Gly
        130                 135                 140

Arg Leu Gly Ala Ala Lys Leu Arg His Ser Lys Gly Cys Asn Cys Lys
145                 150                 155                 160

Arg Ser Gly Cys Leu Lys Asn Tyr Cys Glu Cys Tyr Glu Ala Lys Ile
                165                 170                 175

Met Cys Ser Ser Ile Cys Lys Cys Ile Ala Cys Lys Asn Tyr Glu Glu
            180                 185                 190

Ser Pro Glu Arg Lys Met Leu Met Ser Thr Pro His Tyr Met Glu Pro
        195                 200                 205

Gly Asp Phe Glu Ser Ser His Tyr Leu Ser Pro Ala Lys Phe Ser Gly
    210                 215                 220

Pro Pro Lys Leu Arg Lys Asn Arg Gln Ala Phe Ser Cys Ile Ser Trp
225                 230                 235                 240
```

```
Glu Val Val Glu Ala Thr Cys Ala Cys Leu Leu Ala Gln Gly Glu Glu
                245                 250                 255

Ala Glu Gln Glu His Cys Ser Pro Ser Leu Ala Glu Gln Met Ile Leu
            260                 265                 270

Glu Glu Phe Gly Arg Cys Leu Ser Gln Ile Leu His Ile Glu Phe Lys
        275                 280                 285

Ser Lys Gly Leu Lys Ile Glu
    290                 295

<210> SEQ ID NO 5
<211> LENGTH: 299
<212> TYPE: PRT
<213> ORGANISM: Homo sapiens

<400> SEQUENCE: 5

Met Val Ile Cys Gln Leu Lys Gly Gly Thr Gln Met Leu Cys Ile Asp
 1               5                  10                  15

Asn Ser Arg Thr Arg Glu Leu Lys Ala Leu His Leu Val Pro Gln Tyr
            20                  25                  30

Gln Asp Gln Asn Asn Tyr Leu Gln Ser Asp Val Pro Lys Pro Met Thr
        35                  40                  45

Ala Leu Val Gly Arg Phe Leu Pro Ala Ser Thr Lys Leu Asn Leu Ile
    50                  55                  60

Thr Gln Gln Leu Glu Gly Ala Leu Pro Ser Val Val Asn Gly Ser Ala
65                  70                  75                  80

Phe Pro Ser Gly Ser Thr Leu Pro Gly Pro Pro Lys Ile Thr Leu Ala
                85                  90                  95

Gly Tyr Cys Asp Cys Phe Ala Ser Gly Asp Phe Cys Asn Asn Cys Asn
            100                 105                 110

Cys Asn Asn Cys Cys Asn Asn Leu His His Asp Ile Glu Arg Phe Lys
        115                 120                 125

Ala Ile Lys Ala Cys Leu Gly Arg Asn Pro Glu Ala Phe Gln Pro Lys
    130                 135                 140

Ile Gly Lys Gly Gln Leu Gly Asn Val Lys Pro Gln His Asn Lys Gly
145                 150                 155                 160

Cys Asn Cys Arg Arg Ser Gly Cys Leu Lys Asn Tyr Cys Glu Cys Tyr
                165                 170                 175

Glu Ala Gln Ile Met Cys Ser Ser Ile Cys Lys Cys Ile Gly Cys Lys
            180                 185                 190

Asn Tyr Glu Glu Ser Pro Glu Arg Lys Thr Leu Met Ser Met Pro Asn
        195                 200                 205

Tyr Met Gln Thr Gly Gly Leu Glu Gly Ser His Tyr Leu Pro Pro Thr
    210                 215                 220

Lys Phe Ser Gly Leu Pro Arg Phe Ser His Asp Arg Arg Pro Ser Ser
225                 230                 235                 240

Cys Ile Ser Trp Glu Val Val Glu Ala Thr Cys Ala Cys Leu Leu Ala
                245                 250                 255

Gln Gly Glu Glu Ala Glu Lys Glu His Cys Ser Lys Cys Leu Ala Glu
            260                 265                 270

Gln Met Ile Leu Glu Glu Phe Gly Arg Cys Leu Ser Gln Ile Leu His
        275                 280                 285

Thr Glu Phe Lys Ser Lys Gly Leu Lys Met Glu
    290                 295
```

```
<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 6
ggagaatctg cgacaggcac                                               20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 7
tccccagcca agttctcsgg                                               20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 8
ttcattgacc tcaactacat g                                             21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 9
gtggcagtga tggcatggac                                               20

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 10
tatgggcgcc tcctttcagc tgacaaat                                      28

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 11
actgaggaag cagatggagc gctttgag                                      28

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Primer
```

```
<400> SEQUENCE: 12
tgactgaggg aaactgctct ggtcat                                              26

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 13
aacctgatgg ctggcttgat                                                    20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 14
tttttcttta ctttccttgg                                                    20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 15
ccgaagaagg gctccaagaa                                                    20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 16
tctccactca agacaagcct                                                    20

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 17
tgggcccagg gagtttactc a                                                  21

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 18
tctcccagga ctatgggaac ccaa                                               24

<210> SEQ ID NO 19
<211> LENGTH: 33
```

```
<212> TYPE: DNA
<213> ORGANISM: Artificial Sequence
<220> FEATURE:
<223> OTHER INFORMATION: Description of Artificial Sequence: Primer

<400> SEQUENCE: 19
tcgaattcta tggtgatttg tcagctgaaa gga                                      33

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 20
gaattcgaat tcgcattccc ctttaccagc tt                                       32

<210> SEQ ID NO 21
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 21
accgtcgact gcctaaggtc ctgagaactt ggctgggga                                39

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Cys Leu Ser Gln Ile Leu His Ile Glu Phe Lys Ser Lys Gly Leu Lys
 1               5                  10                  15

Ile Glu

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (2)
<223> OTHER INFORMATION: Arbitrary amino acid
<221> NAME/KEY: MOD_RES
<222> LOCATION: (4)..(12)
<223> OTHER INFORMATION: Arbitrary amino acid
<221> NAME/KEY: MOD_RES
<222> LOCATION: (14)
<223> OTHER INFORMATION: Arbitrary amino acid

<400> SEQUENCE: 23

Cys Xaa Cys Xaa Xaa Xaa Xaa Xaa Xaa Xaa Xaa Xaa Cys Xaa Cys
 1               5                  10                  15

<210> SEQ ID NO 24
<211> LENGTH: 295
<212> TYPE: PRT
<213> ORGANISM: Mus sp.

<400> SEQUENCE: 24
```

-continued

```
Met Val Ile Cys Gln Leu Lys Gly Gly Ala Gln Met Leu Cys Ile Asp
 1               5                  10                  15

Asn Cys Gly Ala Arg Glu Leu Lys Ala Leu His Leu Leu Pro Gln Tyr
                 20                  25                  30

Asp Asp Gln Ser Ser Phe Pro Gln Ser Glu Leu Pro Lys Pro Met Thr
             35                  40                  45

Thr Leu Val Gly Arg Leu Leu Pro Val Pro Ala Lys Leu Asn Leu Ile
         50                  55                  60

Thr Gln Val Asp Asn Gly Ala Leu Pro Ser Ala Val Asn Gly Ala Ala
 65                  70                  75                  80

Phe Pro Ser Gly Pro Ala Leu Gln Gly Pro Pro Lys Ile Thr Leu Ser
                 85                  90                  95

Gly Tyr Cys Asp Cys Phe Ser Ser Gly Asp Phe Cys Asn Ser Cys Ser
             100                 105                 110

Cys Asn Asn Leu Arg His Glu Leu Glu Arg Phe Lys Ala Ile Lys Ala
             115                 120                 125

Cys Leu Asp Arg Asn Pro Glu Ala Phe Gln Pro Lys Met Gly Lys Gly
             130                 135                 140

Arg Leu Gly Ala Ala Lys Leu Arg His Ser Lys Gly Cys Asn Cys Lys
145                 150                 155                 160

Arg Ser Gly Cys Leu Lys Asn Tyr Cys Glu Cys Tyr Glu Ala Lys Ile
                 165                 170                 175

Met Cys Ser Ser Ile Cys Lys Cys Ile Ala Cys Lys Asn Tyr Glu Glu
                 180                 185                 190

Ser Pro Glu Arg Lys Met Leu Met Ser Thr Pro His Tyr Met Glu Pro
             195                 200                 205

Gly Asp Phe Glu Ser Ser His Tyr Leu Ser Pro Ala Lys Phe Ser Gly
             210                 215                 220

Pro Pro Lys Leu Arg Lys Asn Arg Gln Ala Phe Ser Cys Ile Ser Trp
225                 230                 235                 240

Glu Val Val Glu Ala Thr Cys Ala Cys Leu Leu Ala Gln Gly Glu Glu
                 245                 250                 255

Ala Glu Gln Glu His Cys Ser Pro Ser Leu Ala Glu Gln Met Ile Leu
             260                 265                 270

Glu Glu Phe Gly Arg Cys Leu Ser Gln Ile Leu His Ile Glu Phe Lys
             275                 280                 285

Ser Lys Gly Leu Lys Ile Glu
290                 295
```